United States Patent [19]

Pesante et al.

[11] Patent Number: 5,570,407
[45] Date of Patent: Oct. 29, 1996

[54] DISTORTIONLESS X-RAY INSPECTION

[75] Inventors: Eduardo Pesante, Melbourne; Terry Hammond, Palm Bay; Gordon DeBoer, Satellite Beach, all of Fla.

[73] Assignee: Harris Corporation, Melbourne, Fla.

[21] Appl. No.: 268,417

[22] Filed: Jun. 30, 1994

[51] Int. Cl.⁶ .................................................. G01N 23/04
[52] U.S. Cl. ............................ 378/58; 378/57; 378/208
[58] Field of Search .............................. 378/51, 57, 58, 378/62, 204, 208, 209

[56] References Cited

U.S. PATENT DOCUMENTS 2,356,358  8/1944  Schneeman ........................ 378/58 X
4,872,187  10/1989  Nakahata et al. ...................... 378/58 X

*Primary Examiner*—David P. Porta
*Attorney, Agent, or Firm*—Joel I. Rosenblatt

[57] ABSTRACT

The cavities of IC's are inspected for contaminants rising a point source x-ray. The IC's are arranged on a curved surface, approximating the arc formed by the radiation from the point source x-ray. In this way, the IC's may be stood on end with the sides parallel to the x-ray radiation. In this arrangement, the radiation from the x-ray point source passes approximately parallel to the IC size and a clear image of the cavity is achieved without distortion produced by the x-rays passing thou the bottom or the top. Alternately, the curved surface for mounting the IC's may be formed of small straight sections formed at angles approximating the curve.

3 Claims, 3 Drawing Sheets

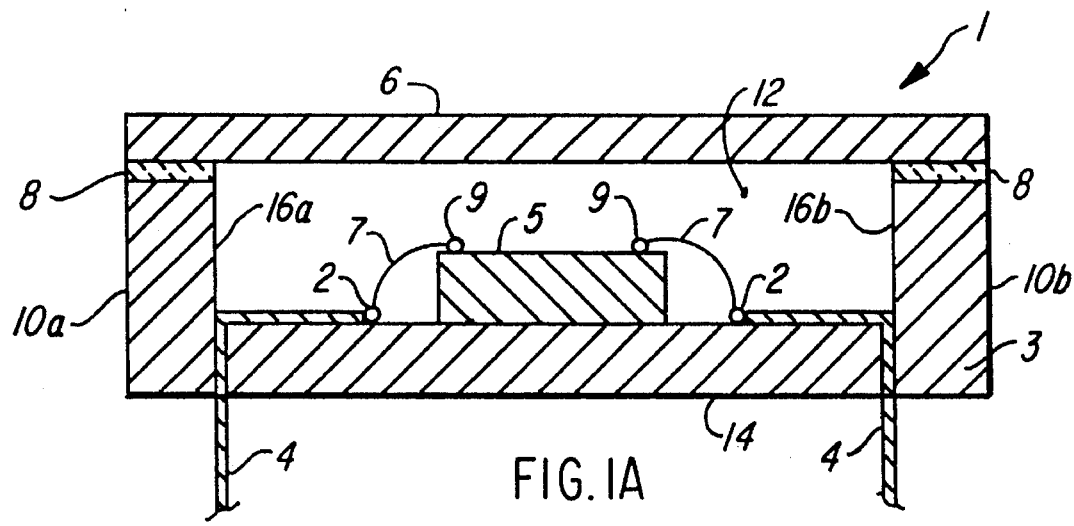
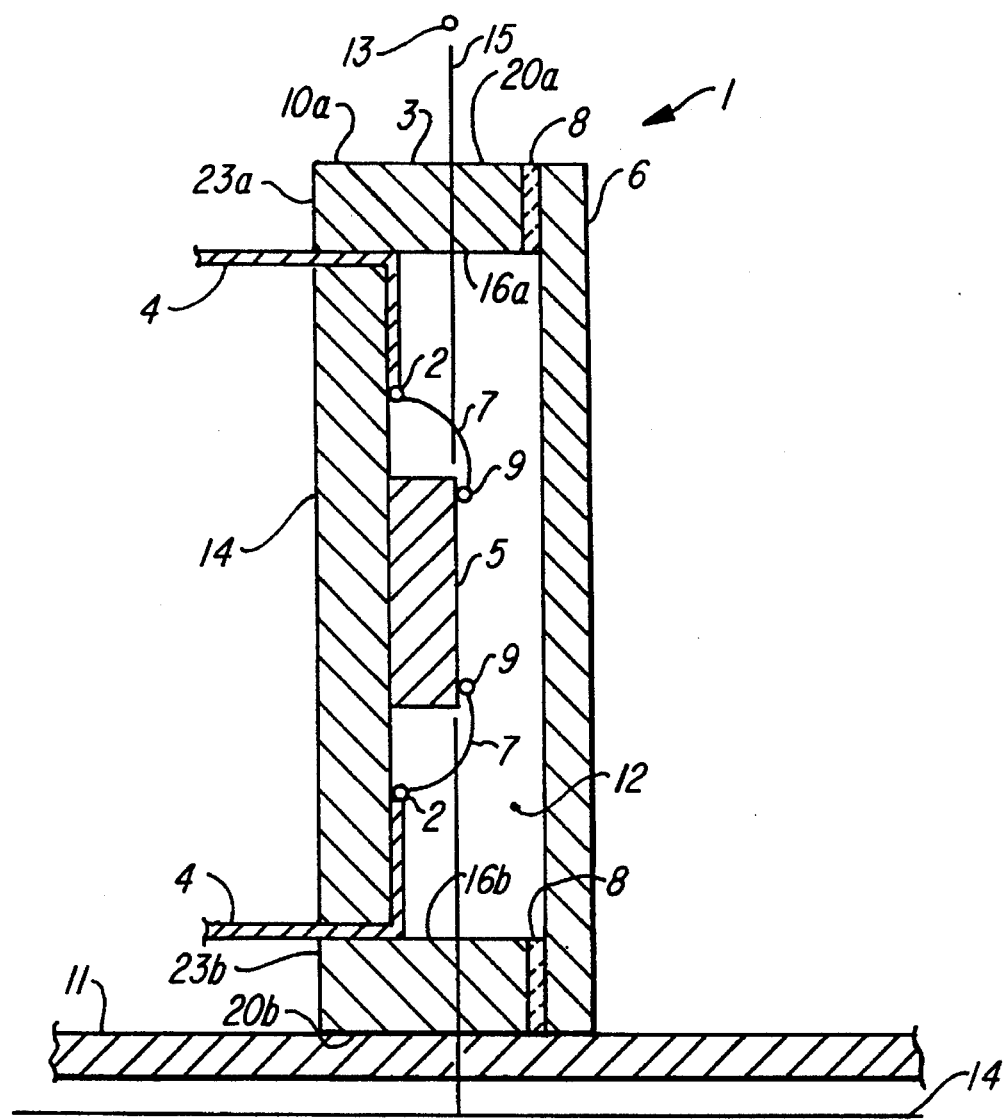
FIG. 1A
FIG. 1B

DISTORTIONLESS X-RAY INSPECTION

FIELD OF THE INVENTION

This invention relates to the inspection of multiple ceramic packages containing integrated circuits on dies and the manner of using a single point of radiation for inspection of these packages without distortion.

BACKGROUND OF THE INVENTION

A sealed integrated circuit typically comprises a ceramic package containing a cavity. The package contains leads extending from the package externally for connection with printed circuit boards or other IC packages. The die containing the electrical circuit is made with bond pads. The die is placed in the ceramic package cavity and the bond die pads are connected to the bond pads in the ceramic package, which in turn are connected to the external leads. The ceramic package is then sealed with a lid placed over the ceramic package, and the die in the cavity. The seal typically may be glass.

In the production of these completed integrated circuits, it is important none of the glass sealant enter into the cavity. The completely packaged integrated circuit may be tested by removing the lid to inspect the cavity for contaminants such as from the glass seal. However, as will be recognized by those skilled in the art, this would be destructive of the IC which would have to be resealed or discarded.

A point source of x-rays has been used to radiate the seal in the ceramic package and produce an image on a plate, Inspection of the plate then would reveal whether any contaminants were allowed to enter the cavity resulting in rejection of the IC.

However, in the prior art, testing of a number of IC packages was prevented by the length formed by line of such tested ICs and the angles formed by the x-ray radiation from the point source on the ICs at the extreme ends of that line. In order to produce a plate by x-ray radiation, which accurately would disclose contaminants in the cavity, it was necessary the x-ray energy source be substantially perpendicular to the IC. This is critical when the IC is placed on an edge and the x-ray radiation is directed to pass through the cavity from side to side to an x-ray sensitive plate. It is important for the x-ray radiation to be substantially perpendicular to the IC so the radiation is directed through the cavity to a plate which records any contaminants in the cavity.

Where the x-ray radiation is not perpendicular to the IC cavity, distortion is produced and the measurement is ineffective.

SUMMARY OF THE INVENTION

As shown in the preferred embodiment according to the inventive principles, a number of ICs are irradiated with x-ray radiation from a point source to determine whether any contaminants are present within a cavity in the ceramic package housing a die and forming the IC.

In the sealing process, the die is placed in a ceramic package cavity as is well known in the art. That ceramic package is sealed with a lid using a sealing substance such as glass. It is important in the sealing process that no glass contaminants enter the cavity.

It is important to be able to irradiate the largest number of IC packages from a single point source to gain the most efficiency in the examination for contaminants in the ceramic package cavity. Radiation from a point source, radiates in an arc. The radiation is perpendicular to a object placed anywhere along the arc. Where objects such as ICs are placed on a plane, tangential to the arc, the radiation is perpendicular to the object placed at that tangent, and is at an angle to any other object placed on that plane. The farther from the tangential point of contact of the plane with the arc, the more acute the angle formed by the radiation and the object on that plane.

Accordingly, as objects for radiation are placed on the plane, the further the object on that plane from the center object, the more of an angle formed by the x-ray radiation from that point source on that object.

Accordingly, a limit is placed on a number of objects that may be irradiated by a point source of x-ray radiation where that measurement requires the angle formed by the radiation with the object be substantially perpendicular.

According to the inventive principles as shown in the preferred embodiment, the number of objects which are irradiated with x-ray radiation from a point source for the purpose of testing to determine contaminants in a cavity may be extended. In the testing of an integrated circuit formed by a die placed in a cavity within a ceramic package and covered by a lid sealed with a sealant such as glass for example, it is important to be able to expose the cavity within the ceramic to radiation passing from side to side through the cavity. This is in distinction to radiation passing from the open side of the cavity covered by the lid through the ceramic package and out through the bottom of the ceramic package. When ICs are irradiated using x-ray energy, the perpendicular alignment of the IC ceramic package cavity exposed through its sides to the point source of x-ray radiation becomes critical. According to the inventive principles, this invention achieves this perpendicular alignment along the line of integrated circuits with each integrated circuit exposed to the radiation through its ceramic package cavity sides, by placing the ICs on a platform arranged in a curve or with straight portions linked to each other at angles and resembling a curve and conforming to the arc of the x-ray radiation from the point source.

Where linked flat portions are used, arranged with angles to each other resembling the arc formed by the radiation from the point source, each of the ICs are substantially perpendicular to the radiation. It is recognized that exact perpendicularity is not essential but the angle of incidence of the radiation from the point source with the ICs may vary about 90°. It is important the point source x-rays be substantially perpendicular so the radiation passes through the IC sides and is not distorted by the IC bottom or sealing lid.

Additionally, holders may be provided to support the objects for radiation where the angle formed by the curved surface supporting the objects put the objects at an incline causing instability.

DESCRIPTION OF THE DRAWINGS

FIG. 1a shows an IC in cross section.

FIG. 1b shows the preferred way of examining the cavity in the IC of FIG. 1a.

DESCRIPTION OF PREFERRED EMBODIMENT

Figure 2A:
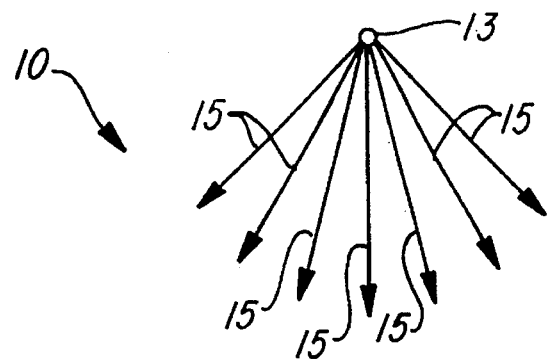
FIG. 2a shows the prior art method of testing using a point source of radiation and with the tested objects to be irradiated arranged on a plane.
Figure 2A:
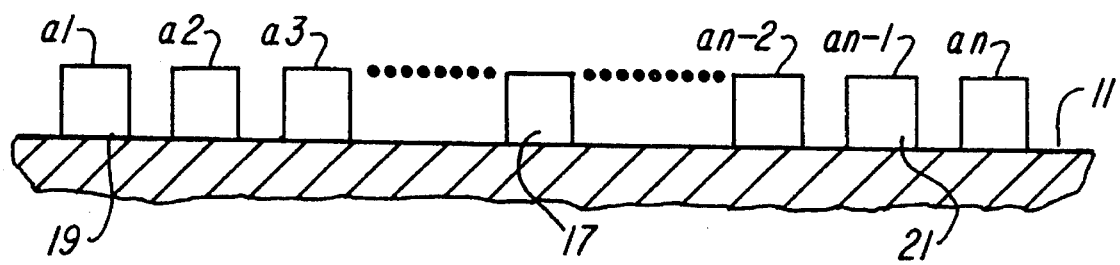

Referring now to FIG. 1a, an integrated circuit ("IC") is denoted generally by numeral 1. A ceramic package 3 contains a cavity 12. Within the cavity is a die 5 containing bond pads 9. Bond pad 9 is connected by wires set 7 into individual leads 2 within the ceramic package bond frame as indicated by numeral 4. The ceramic package is sealed to form the IC by lid 6. Lid 6 is sealed to the ceramic package 3 by sealant 8. As known to those skilled in the art, the sealant may be for example glass. The package 3 includes sides 23a, 23b defined by exterior walls 10a, 10b and interior walls 16a, 16b, and bottom 14.

in the manufacture of IC packages, it is important that the sealant not enter the cavity 12 forming contaminants within that cavity.

Figure 4:
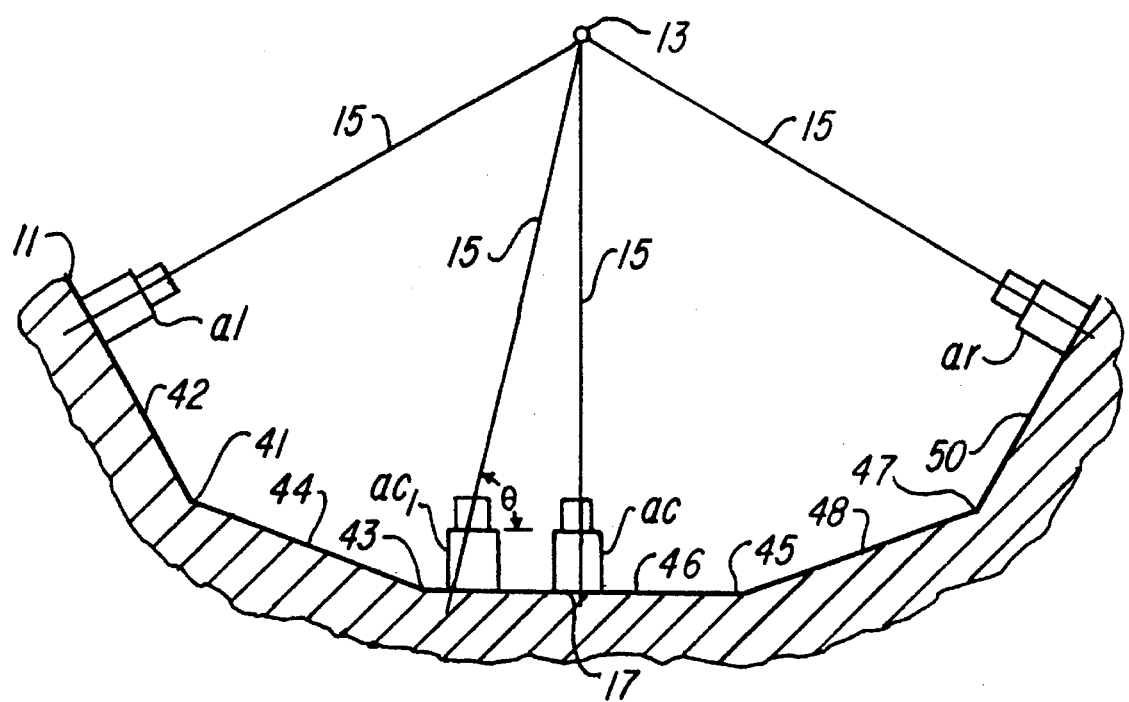
FIG. 4. shows a variation of the platform shown in FIG. 3. where the platform is formed of straight sections arranged at angles to each other to resemble the arc produced by the radiation from a point source.

The preferred way of examining the cavity 12 within the IC for contaminants as is shown in FIG. 4 with the IC placed on its edge and the x-ray radiation 15 from point source 13 passing through the sides 23a and 23b of the ceramic package 3 and through the cavity 12 as shown in FIG. 1b.

Figure 2B:
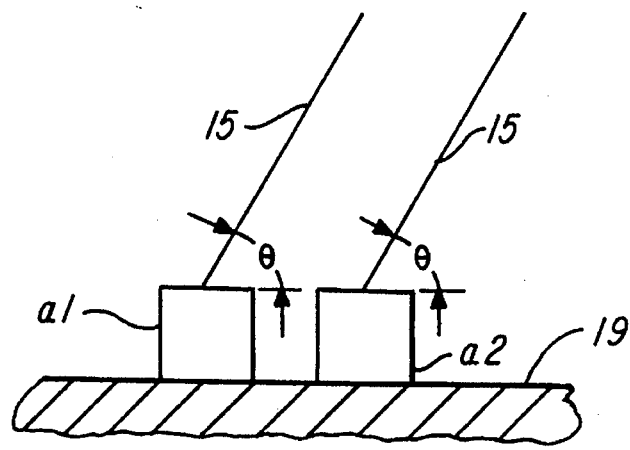
FIG. 2b shows a detail of FIG. 2a showing the angle formed by the radiation with the objects to be tested.

FIG. 2a shows a prior art method and apparatus for x-ray examination of ICs 91 to an placed on a flat surface 11 extending from points 19 to points 21. The point source of x-ray radiation is indicated by 13 with the radiation extending in an arc from that point source indicated by the arrows 15. As seen by inspection, the radiation 15 from point source 13 will be most nearly perpendicular to the ICs located around point 17, directly under the point source. This point 17 may be thought of as a tangent to the arc formed by the radiation from point source 15. Along the ends of the flat surface 11 towards the left as shown by IC a1 or the end 2 to the right as shown by IC an, the angle θ formed by the radiation from point source 13 becomes more acute as shown by angle in FIG. 2b for a1 and a2. As would be understood by those skilled in the art, the angle θ formed for IC a2 would be closer to the perpendicular but only slightly so, compared to the angle θ formed by the radiation and IC a1.

Figure 3:
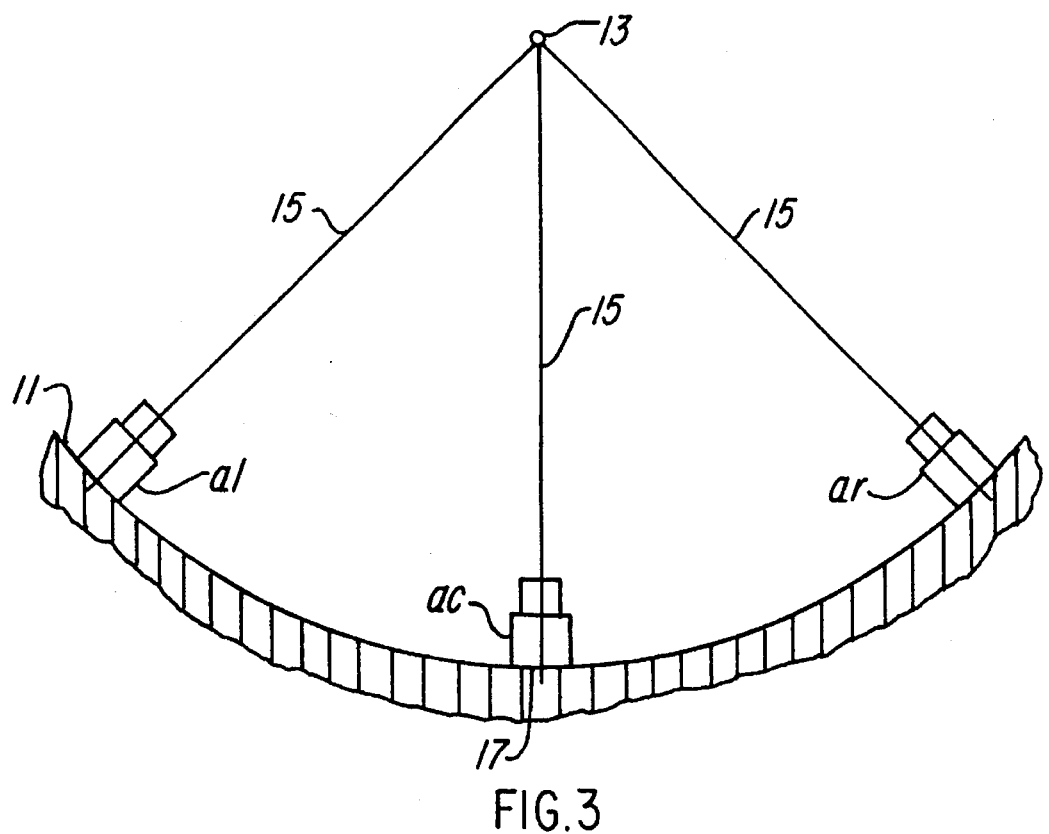
FIG. 3. shows the preferred embodiment according to the inventive principles of a testing platform arranged to resemble the arc formed by the radiation from a point source.

The preferred embodiment according to the inventive principles is shown in FIG. 3. As shown, the surface 11 supporting the ICs is curved resembling the arc formed by the shaped of the radiation 15 from point source 13. The series of ICs placed on the support 17 are represented by an extreme left IC a1, a middle ac placed in the middle of support 11 along its arcuate surface, and a right most IC denoted by ar.

As shown in FIG. 3., the beam from the point source 13 shown by arrows 15, is perpendicular to the ICs and pass directly through the cavities as shown in FIG. 1b.

In FIG. 1b, the IC of FIG. 1a is shown on its sides 23a, 23b exposed to beam 15 from point source 13. The support shown as 11, beneath the support 11 is a radiation sensitive plate such as an x-ray plate 14.

As shown is FIG. 1b, the beam 15 from point source 13 passes through the exterior side 10a of side 23a, entering the cavity 12 through its interior side 16a, passing through the cavity 3 through side 23b interior side 16b, through its exterior side 10b, through support 11, and to plate 14. In this way, a reading of the contents of the cavity 12 can be obtained without distortion produced by the lid 6 or bottom 14 by aligning the IC on a surface substantially aligned with the arc of the radiation from the point source.

An alternate arrangement for the arcuate or curved platform 11 is shown is FIG. 4. In FIG. 4, the platform is composed of straight supports such as 42, 44, 46, 48, and 50, joined to each other at points 41, 43, 45, and 47 respectively. The angle formed by the radiation 15 from the point source 13 is substantially perpendicular along each of the straight sections, 42, 44, 46, 48, and 50. A sufficient angle is placed at the points of intersection 41, 43, 45, and 47, to make each of the ICs on each of the respective sections align substantially perpendicularly with the radiation 15 from point source 13.

In constructing a platform 11, it is necessary to first determine the range of angles around the perpendicular which can be tolerated to produce a sufficiently accurate plate or exposure from a beam passing through the cavity 12 of IC 1. The platform may then be made by any suitable method, known to those skilled in the art to be curved. The curve may be continuous as shown in FIG. 3. or it may be discontinuous curve made of straight lines, as shown in FIG. 4. The length of each of the straight supports 42, 44, 46, 48, 50, and the conformance of the platform 11 curve to the arc formed by the radiation from point source 13 will depend upon the degree of tolerance from the perpendicular allowed for the application. For example, where a tolerance to the perpendicular from 85° to 95°, may be tolerated, then the surface may be extended in a straight line, for example between points 43 and 45 so the distance of IC ac 1 from center location 17 causes the angle θ formed by the x-ray beam 15 to be greater than 85°.

As the methods of manufacture of support 11 to provide the proper angular relationship to point source 13 are well known, it is not discussed in detail.

We claim:

1. An apparatus for accurately inspecting a sealed cavity of an IC for contaminants in the cavity comprising:

an IC having a cavity defined by a lid, a bottom a first side wall and a second side wall;

a point source of radiation;

said lid said IC being sealed to said first wall and said second wall by sealing means;

radiation sensitive means placed on the opposite side of said IC from said point source of radiation; whereby, said cavity to said radiation sensitive means; and means for aligning said IC relative to said point source at radiation to pass radiation from said point source of radiation perpendicularly through said cavity and said first side wall and second side wall, to said radiation sensitive means without passing through said lid or said bottom, to form an image of said cavity unobstructed by said lid or bottom;

said point source of radiation is arranged to emit an arcuate wave front; and said means for aligning is arranged to be arcuate in the shape of said arcuate wave front.

2. The apparatus of claim 1, wherein:

said means for aligning is continuously arcuate.

3. The apparatus of claim 1, wherein:

said means for aligning is arranged as flat sections connected at an angle with adjoining flat sections and said connected flat sections form a discontinuous arcuate surface.

* * * * *